(12) United States Patent
Cahoon et al.

(10) Patent No.: US 6,465,234 B2
(45) Date of Patent: Oct. 15, 2002

(54) N-END RULE PATHWAY ENZYMES

(75) Inventors: Rebecca E. Cahoon, Wilmington; Saverio Carl Falco, Ardern; J. Antoni Rafalski; Hajime Sakai, both of Wilmington, all of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/921,259

(22) Filed: Aug. 2, 2001

(65) Prior Publication Data

US 2002/0086388 A1 Jul. 4, 2002

Related U.S. Application Data

(62) Division of application No. 09/370,807, filed on Aug. 9, 1999, now Pat. No. 6,297,034.
(60) Provisional application No. 60/096,225, filed on Aug. 12, 1998.

(51) Int. Cl.[7] .............................. C12N 9/50; C07H 21/04
(52) U.S. Cl. ...................... 435/219; 435/183; 435/410; 435/419; 435/252.3; 435/320.1; 435/180; 435/325; 435/254.2; 435/440; 536/23.1; 536/23.2; 536/23.6; 800/295; 800/278
(58) Field of Search ................................. 435/219, 183, 435/410, 419, 252.3, 320.1, 180, 325, 440; 536/23.1, 23.2, 23.6; 800/295, 278

(56) References Cited

PUBLICATIONS

Kwon et al., (1999), Mol. Cell Biol., 19:182–193.
NCBI General Identifier No. 4313355 (1999).
Koster et al., (1995), Mol. Biol. Rep., 21:11–20.
Falquet et al., (1995) FEBS Lett. 376:233–237.
Falquet et al., (1995) FEBS Lett. 359:73–77.
Hadari et al., (1992) J. Biol. Chem. 267:719–727.
NCBI General Identifier No. 4688518 (1999).
NCBI General Identifier No. 3768668 (1998).
NCBI General Identifier No. 701567 (1995).
NCBI General Identifier No. 417633 (1994).
Wardhan et al. Gene, 121(1), 133–136 (1992).
NCBI General Identifier No. 5103048 (1999).
Dumay et al. Microbiology 145, 1275–1285, (1999).
NCBI General Identifier No. 2499137 (1997).
Brookman et al. Genomics, 22(1), 180–188, (1994).
NCBI General Identifier No. 585481 (1998).
Ogasawara et al. DNA Res. 1(1), 1–14, (1994).
NCBI General Identifier No. 3914015 (1998).
Kaneko et al. DNA Res. 2(4), 153–166, (1995).

*Primary Examiner*—Rebecca E. Prouty
*Assistant Examiner*—Richard Hutson

(57) ABSTRACT

This invention relates to an isolated nucleic acid fragment encoding an enzyme involved in the N-end rule pathway of protein degradation. The invention also relates to the construction of a chimeric gene encoding all or a portion of the enzyme involved in the N-end rule pathway of protein degradation, in sense or antisense orientation, wherein expression of the chimeric gene results in production of altered levels of the enzyme involved in the N-end rule pathway of protein degradation in a transformed host cell.

13 Claims, No Drawings

N-END RULE PATHWAY ENZYMES

This application is a divisional of Ser. No. 09/370,809, filed Aug. 9, 1999, which issued as U.S. Pat. No. 6,297,034 and claims the benefit of U.S. Provisional Application No. 60/096,225, filed Aug. 12, 1998.

FIELD OF THE INVENTION

This invention is in the field of plant molecular biology. More specifically, this invention pertains to nucleic acid fragments encoding enzymes involved in the N-end rule pathway of protein degradation in plants and seeds.

BACKGROUND OF THE INVENTION

Cells continuously synthesize proteins from and degrade them into their component amino acids. The function of this seemingly wasteful process is twofold: first, to eliminate abnormal proteins whose accumulation would be harmful to the cell, and second, to permit the regulation of cellular metabolism by eliminating superfluous enzymes and regulatory proteins. The level of an enzyme depends on its rate of degradation as well as its rate of synthesis. Non-selective protein degradation occurs by a lysosomal mechanism. In eukaryotes a cytosolic ATP-dependent mechanism of protein degradation involves ubiquitin. This mechanism is based on the protein's half life which is partially determined by its N-terminal residue, giving this degradation mechanism the name of N-end rule pathway. The enzymes included in this application are involved in the N-end rule pathway of protein degradation.

Arginyl-tRNA-protein transferase (EC 2.3.2.8) is involved in catalyzing the post-translational conjugation of arginine to the amino termini of acceptor proteins. The function of these enzymes in eukaryotes is apparently to conjugate destabilizing amino acids to the amino termini of short-lived proteins. This reaction is a part of the N-end rule pathway of protein degradation. *Arabidopsis thaliana* encodes a single form of arginyl-tRNA-protein transferase while two forms, which are differentially spliced, are encoded by mice and humans (Kwon et al. (1999) *Mol. Cell. Biol.* 19:182–193). A soybean EST encoding a peptide with similarities to cDNAs encoding arginyl-tRNA-protein transferase is found in the NCBI EST database having NCBI General Identifier No. 4313355.

The 26S proteosome is the central protease of the ubiquitin-dependent pathway of protein degradation. The 26S proteosome is formed by a barrel-shaped 20S core complex and two polar 19S complexes. The 20S particle contains the protease activity while the 19S complex contains isopeptidase, ATPase, and protein unfolding activities (Koster et al. (1995) *Mol. Biol. Rep.* 21:11–20). Isopeptidases, also called ubiquitin carboxy-terminal hydrolases, belong to a family containing at least 10 different members. A 100 kDa de-ubiquitinating enzyme isolated from human tissues has been shown to contain "His and Cys domains" which are likely involved in the de-ubiquitinating activity, and an aspartic acid domain of unknown function Falquet et al. (1995) *FEBS Lett.* 376:233–237. Because this enzyme cleaves peptide-linked and isopeptide-linked ubiquitin moieties from substrates, it is considered a de-ubiquitinase, instead of a isopeptidase (Falquet et al. (1995) *FEBS Lett.* 359:73–77). An alignment of de-ubiquitinating enzymes shows that de-ubiquitinase is 99% similar to isopeptidase T. De-ubiquitinase contains a 23 amino acid insertion at position 629 of isopeptidase T which may account for the difference in activity between the two enzymes. Isopeptidase T is a monomeric ubiquitin-binding protein whose activity is inhibited by iodoacetamide and ubiquitin aldehyde (Hadari et al. (1992) *J. Biol. Chem.* 267:719–727). A corn EST encoding a peptide with similarities to cDNAs encoding isopeptidase T is found in the NCBI database having NCBI General Identifier No. 4688518. Rice ESTs encoding peptides with similarities to cDNAs encoding isopeptidase T are found in the NCBI database having NCBI General Identifier Nos. 3768668 and 701567.

SUMMARY OF THE INVENTION

The instant invention relates to isolated nucleic acid fragments encoding enzymes involved in the N-end rule pathway of protein degradation. Specifically, this invention concerns an isolated nucleic acid fragment encoding an arginyl-tRNA-protein transferase or an isopeptidase T and an isolated nucleic acid fragment that is substantially similar to an isolated nucleic acid fragment encoding an arginyl-tRNA-protein transferase or an isopeptidase T. In addition, this invention relates to a nucleic acid fragment that is complementary to the nucleic acid fragment encoding arginyl-tRNA-protein transferase or isopeptidase T.

An additional embodiment of the instant invention pertains to a polypeptide encoding all or a substantial portion of an enzyme involved in the N-end rule pathway of protein degradation selected from the group consisting of arginyl-tRNA-protein transferase and isopeptidase T.

In another embodiment, the instant invention relates to a chimeric gene encoding an arginyl-tRNA-protein transferase or an isopeptidase T, or to a chimeric gene that comprises a nucleic acid fragment that is complementary to a nucleic acid fragment encoding an arginyl-tRNA-protein transferase or an isopeptidase T, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an arginyl-tRNA-protein transferase or an isopeptidase T, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an arginyl-tRNA-protein transferase or an isopeptidase T in a transformed host cell comprising: a) transforming a host cell with a chimeric gene comprising a nucleic acid fragment encoding an arginyl-tRNA-protein transferase or an isopeptidase T; and b) growing the transformed host cell under conditions that are suitable for expression of the chimeric gene wherein expression of the chimeric gene results in production of altered levels of arginyl-tRNA-protein transferase or isopeptidase T in the transformed host cell.

An addition embodiment of the instant invention concerns a method for obtaining a nucleic acid fragment encoding all or a substantial portion of an amino acid sequence encoding an arginyl-tRNA-protein transferase or an isopeptidase T.

A further embodiment of the instant invention is a method for evaluating at least one compound for its ability to inhibit the activity of an arginyl-tRNA-protein transferase or an isopeptidase T, the method comprising the steps of: (a) transforming a host cell with a chimeric gene comprising a nucleic acid fragment encoding an arginyl-tRNA-protein transferase or an isopeptidase T, operably linked to suitable regulatory sequences; (b) growing the transformed host cell under conditions that are suitable for expression of the chimeric gene wherein expression of the chimeric gene results in production of arginyl-tRNA-protein transferase or isopeptidase T in the transformed host cell; (c) optionally purifying the arginyl-tRNA-protein transferase or the isopeptidase T expressed by the transformed host cell; (d) treating the arginyl-tRNA-protein transferase or the isopeptidase T with a compound to be tested; and (e) comparing the activity of the arginyl-tRNA-protein transferase or the isopeptidase T that has been treated with a test compound to the activity of an untreated arginyl-tRNA-protein transferase or isopeptidase T, thereby selecting compounds with potential for inhibitory activity.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the

TABLE 1

Enzymes Involved in the N-End Rule Pathway of Protein Degradation

| Protein | Clone Designation | SEQ ID NO: (Nucleotide) | SEQ ID NO: (Amino Acid) |
|---|---|---|---|
| Soybean arginyl-tRNA-protein transferase | ses2w.pk0008.d11 | 1 | 2 |
| Wheat arginyl-tRNA-protein transferase | wr1.pk0035.f3 | 3 | 4 |
| Corn isopeptidase T | cc3.pk0006.b12 | 5 | 6 |
| Rice isopeptidase T | rr1.pk0049.c1 | 7 | 8 |
| Corn isopeptidase T | Contig of: cen3n.pk0018.e1 cen3n.pk0032.f11 | 9 | 10 |
| Soybean isopeptidase T | Contig of: sdp3c.pk019.c18 ss1.pk0036.b8 | 11 | 12 |
| Wheat isopeptidase T | wdk5c.pk0001.d10 | 13 | 14 |
| Wheat isopeptidase T | w1m0.pk042.e15 | 15 | 16 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several enzymes involved in the N-end rule pathway of protein degradation have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other arginyl-tRNA-protein transferases or isopeptidase Ts, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1 984) *Adv. Immunol.* 36:1; Maniatis).

The nucleic acid fragments of the instant invention may be used to create transgenic plants in which the disclosed polypeptides are present at present at higher or lower levels than normal or in cell types or developmental stages in which they are not normally found. This would have the effect of altering the level of protein degradation in those cells. Prolonging the half-life of short-lived proteins may lead to cell proliferation which could then increase the rate of growth of the plants.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded enzymes involved in the N-end rule pathway of protein degradation. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in protein degradation. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cc3 | Corn Callus Embryo | cc3.pk0006.b12 |
| cen3n | Corn Endosperm 20 Days After Pollination* | cen3n.pk0018.e1 cen3n.pk0032 |
| rr1 | Rice Root of Two Week Old Developing Seedling | rr1.pk0049.c1 |
| sdp3c | Soybean Developing Pods (8–9 mm) | sdp3c.pk019.c18 |
| ses2w | Soybean Embryogenic Suspension 2 Weeks After Subculture | ses2w.pk0008.d11 |
| ss1 | Soybean Seedling 5–10 Days After Germination | ss1.pk0036.b8 |
| wdk5c | Wheat Developing Kernel, 30 Days After Anthesis | wdk5c.pk0001.d10 |
| wlm0 | Wheat Seedlings 0 Hour After Inoculation With *Erysiphe graminis f.* sp *tritici* | wlm0.pk042.e15 |
| wr1 | Wheat Root From 7 Day Old Seedling | wr1.pk0035.f3 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10 B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding enzymes involved in the N-end rule pathway of protein degradation were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding a Arginyl-tRNA-Protein Transferase

The BLASTX search using the EST sequences from clones listed in Table 3 revealed similarity of the polypeptides encoded by the cDNAs to arginyl-tRNA-protein transferase from *Arabidopsis thaliana* (NCBI General Identifier No. 3806098). Shown in Table 3 are the BLAST results for individual ESTs ("EST"), or the sequences of the entire cDNA inserts comprising the indicated cDNA clones ("FIS"):

TABLE 3

BLAST Results for Sequences Encoding Polypeptides Homologous to Arginyl-tRNA-Protein Transferase

| Clone | Status | BLAST pLog Score 3806098 |
| --- | --- | --- |
| Ses2w.pk0008.d11 | FIS | 178.00 |
| Wr1.pk0035.f3 | EST | 139.00 |

The data in Table 4 represents a calculation of the percent identity of the amino acid sequences set forth in SEQ ID NOs:2 and 4 and the *Arabidopsis thaliana* (NCBI General Identifier No. 3806098) sequence.

TABLE 4

Percent Identity of Amino Acid Sequences Deduced From the Nucleotide Sequences of cDNA Clones Encoding Polypeptides Homologous to arginyl-tRNA-protein transferase

| SEQ ID NO. | Percent Identity to 3806098 |
| --- | --- |
| 2 | 49.8 |
| 4 | 40.4 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a soybean and a wheat arginyl-tRNA-protein transferases. These sequences represent a soybean variant and the first wheat sequences encoding arginyl-tRNA-protein transferase.

Example 4

Characterization of cDNA Clones Encoding Isopeptidase T

The BLASTX search using the EST sequences from clones listed in Table 5 revealed similarity of the polypeptides encoded by the cDNAs to isopeptidase T from *Homo sapiens* or *Mus musculus* (NCBI General Identifier Nos. 4507855 and 3024764, respectively). Shown in Table 5 are the BLAST results for individual ESTs ("EST"), the sequences of the entire cDNA inserts comprising the indicated cDNA clones ("FIS"), contigs assembled from two or more ESTs ("Contig"), or contigs assembled from an FIS and one or more ESTs ("Contig*"):

TABLE 5

BLAST Results for Sequences Encoding Polypeptides Homologous to Isopeptidase T

| Clone | Status | NCBI General Identifier No. | BLAST pLog Score |
| --- | --- | --- | --- |
| cc3.pk0006.b12 | FIS | 4507855 | 254.00 |
| rr1.pk0049.c1 | FIS | 4507855 | 150.00 |
| Contig of:<br>cen3n.pk0018.e1<br>cen3n.pk0032.f11 | Contig | 3024764 | 33.00 |
| Contig of:<br>sdp3c.pk019.c18<br>ss1.pk0036.b8 | Contig* | 4507855 | 153.00 |
| wdk5c.pk0001.d10 | FIS | 4507855 | 74.30 |
| wlm0.pk042.e15 | EST | 3024764 | 37.40 |

The data in Table 6 represents a calculation of the percent identity of the amino acid sequences set forth in SEQ ID NOs:6, 8, 10, 12, 14 and 16 and the *Homo sapiens* and *Mus musculus* sequences (NCBI General Identifier Nos. 4507855 and 3024764, respectively)

TABLE 6

Percent Identity of Amino Acid Sequences Deduced From the
Nucleotide Sequences of cDNA Clones Encoding Polypeptides
Homologous to Isopeptidase T

| | Percent Identity to | |
|---|---|---|
| SEQ ID NO. | 4507855 | 3024764 |
| 6 | 44.3 | 38.3 |
| 8 | 41.1 | 35.4 |
| 10 | 44.2 | 38.0 |
| 12 | 41.1 | 39.2 |
| 14 | 40.9 | 44.3 |
| 16 | 61.2 | 35.4 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of two corn, a rice, a soybean and two wheat isopeptidase Ts. These sequences represent two variant corn, a variant rice and first soybean and wheat sequences encoding isopeptidase T.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5'and 3'regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature (London)* 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR 225 (from *E. coli;* Gritz. (1983) *Gene* 25:179–188) and the 3'region the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25 °Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating the expected molecular weight.

Example 8

Evaluating Compounds for their Ability to Inhibit the Activity of Enzymes Involved in the N-End Rule Pathway of Protein Degradation The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, an assay for arginyl-tRNA-protein transferase is presented by Gonda et al. (1989) *J. Biol Chem.* 264, 16700–16712. A general assay for isopeptidase is presented by Dang, L. C. et al. (1998) *Biochemistry* 37:1868–1879.

What is claimed is:

1. An isolated polynucleotide comprising:
   (a) a nucleotide sequence encoding a polypeptide having isopeptidase T activity, wherein the amino acid sequence of the polypeptide and the amino acid sequence of SEQ ID NO:6 have at least 80% sequence identity based on the Clustal alignment method, or
   (b) the complement of the nucleotide sequence of (a), wherein the complement and the nucleotide sequence contain the same number of nucleotides and are 100% complementary.

2. The polynucleotide of claim 1 wherein the amino acid sequence of the polypeptide and the amino acid sequence of SEQ ID NO:6 have at least 90% sequence identity based on the Clustal alignment method.

3. The polynucleotide of claim 1 wherein the amino acid sequence of the polypeptide and the amino acid sequence of SEQ ID NO:6 have at least 95% sequence identity based on the Clustal alignment method.

4. The polynucleotide of claim 1 wherein the polypeptide comprises the amino acid sequence of SEQ ID NO:6.

5. The polynucleotide of claim 1 wherein the nucleotide sequence comprises the nucleotide sequence of SEQ ID NO:5.

6. A vector comprising the polynucleotide of claim 1.

7. A recombinant DNA construct comprising the polynucleotide of claim 1 operably linked to at least one regulatory sequence.

8. A method for transforming a cell comprising transforming a cell with the polynucleotide of claim 1.

9. A cell comprising the recombinant DNA construct of claim 7.

10. A method for producing a plant comprising transforming a plant cell with the polynucleotide of claim 1 and regenerating a plant from the transformed plant cell.

11. A plant comprising the recombinant DNA construct of claim 7.

12. A seed comprising the recombinant DNA construct of claim 7.

13. A method for isolating a polypeptide encoded by the polynucleotide of claim 1 comprising isolating the polypeptide from a cell containing a recombinant DNA construct comprising the polynucleotide operably linked to a regulatory sequence.

* * * * *

UNITED STATES PATENT AND TRADEMARK OFFICE
CERTIFICATE OF CORRECTION

| | | |
|---|---|---|
| PATENT NO. | : 6,465,234 B2 | Page 1 of 2 |
| DATED | : October 15, 2002 | |
| INVENTOR(S) | : Rebecca E. Cahoon et al. | |

It is certified that error appears in the above-identified patent and that said Letters Patent is hereby corrected as shown below:

<u>Title page,</u>
Item [75], Inventors, should read as follows:
-- Rebecca E. Cahoon and J. Antoni Rafalski, both of Wilmington, Delaware --.

<u>Column 1,</u>
Line 3, "09/370,809" should read -- 09/370,807 --.

<u>Column 8,</u>
Lines 54 and 55, the word "product (s)" should be -- product(s) --.

<u>Column 9,</u>
Line 18, the word "Agrobacterium" should be -- *Agrobacterium* --.
Line 57, the words "in vitro" should be -- *in vitro* --.

<u>Column 10,</u>
Line 28, the word "be" first occurrence, should be deleted.
Line 30, "(1 984)" should read -- (1984) --.
Line 34, the words "at present" should be deleted.

<u>Column 12,</u>
Lines 3 and 4, "to the these" should read -- to these --.
Line 6, the words "in situ" and "in vitro" should be -- *in situ* -- and -- *in vitro* --.

<u>Column 13,</u>
Line 1, the words "in situ" should be -- *in situ* --.

<u>Column 14,</u>
Line 58, "DH10 B" should read -- DH10B --.

<u>Column 17,</u>
Line 56, "pML 103" should read -- pML103 --.

<u>Column 18,</u>
Line 24, "Pat" should be -- *Pat* --.
Line 28, "pat" should be -- *pat* --.

UNITED STATES PATENT AND TRADEMARK OFFICE
CERTIFICATE OF CORRECTION

PATENT NO. : 6,465,234 B2
DATED : October 15, 2002
INVENTOR(S) : Rebecca E. Cahoon et al.

It is certified that error appears in the above-identified patent and that said Letters Patent is hereby corrected as shown below:

Column 19,
Line 37, "pUC 18" should be -- pUC18 --.
Line 38, "embroys" should be -- embryos --.
Lines 50 and 51, "can maintained" should be -- can be maintained --.
Line 59, "*London*" should be -- London --.
Line 60, "PDS 1000/HE" should be -- PDS1000/HE --.
Line 66, "pJR 225" should be -- pJR225 --.
Line 66, "Gritz." should be -- Gritz et al. --.

Column 21,
Line 23, "(986)" should be -- (1986) --.
Line 50, "in planta" should be -- *in planta* --.
Line 53, "in vivo" should be -- *in vivo* --.

Signed and Sealed this

Twenty-third Day of September, 2003

JAMES E. ROGAN
*Director of the United States Patent and Trademark Office*

SEQUENCE LISTING

<160> NUMBER OF SEQ ID NOS: 16

<210> SEQ ID NO 1
<211> LENGTH: 2060
<212> TYPE: DNA
<213> ORGANISM: Glycine max

<400> SEQUENCE: 1

-continued

```
tgcccccaa aacccaagaa gaaatggcga gtagcagcag caacactccg aaggaaagcg      60
tggttgacga tcggggaagg cgtcgaacct cttgtggcta ttgcagatcc tctcgtgaca    120
atagcatctc tcatggcatg tgggcacata gccttacagt ggatgactac caagatcttc    180
ttgattgtgg ctggagaagg tctggatgtt ttctttataa accagagatg gaaaggacat    240
gctgcccttc ttatacaatt cgcttgaaag caagtaactt tgttccttct aaggagcaac    300
ttcgtgtatc tatacgaatg caaaggtttt tagatggaac cttggatgta aaaaaagtcg    360
atgtcacgga ggacccaacc aaatcaggaa acttctccag tcctatgtca gaagaatcct    420
tagctgctgg cagtgaaaac aaggatgaag ttgaaaaatc tttgcattta tcaaaccaaa    480
ttgataatgt aatacacatc ctcattgaga ggggggaatt tgcctctggt attcaattac    540
caaaagcttc agtgaaaaga gtttcacagg gaaaaaggaa gttactagtc aatggatcag    600
aagatctctt atatagtagc aatatagcct ttcaaattgc agcatctata aaacgagcac    660
aatcatgtga caaggttgtc aatgattcca aaccatcaag agtttgtgaa aaggagaatg    720
attcatctcc taaaattatt gcagaaaagc tagtagcttc tttagatcca actgtgaaaa    780
attctggttt gtctatcagg gcttgcaatg gacatatcaa ttttatgct tctagtaagc     840
aagtttcctt gaacagaagt gttcaaaatg ctccagttcc taaaaattct agaatgaagc    900
attacagtgg aggaaattgt tgattggtc aggtaaaaag gcgaaagctt gagatccgtt     960
taaacagatc cagttttgat ccagaagaat ttgctttgta cagaagatat cagctcaaag   1020
tacataatga taaaccacaa aatgtcacag agaactcata tcgcagtttt ttggttgata   1080
ctccattaat acaagtttct cctactggtg gtagcacagt tcctccttgt ggttttggct   1140
ctttccatca acaatatcta atagatggcc agttagtggc agttggtgtt atagatatcc   1200
ttcccaaatg tttgtcaagt aaatatttgt tctgggatcc agactttgcc tatctatcac   1260
taggcaagta ctcagctttt caagaaatag gttgggtgaa agaaaaccag gtttattgtc   1320
ctagtctaca atactattat cttggctatt atattcactc ttgcaacaag atgagataca   1380
aagctgcata tcacccttca gagctttat gccctcttcg ctatcagtgg ttccatttg     1440
acattgcaag gcctctgctt gacagaaaac cttatgttgt cttatcagat tcttccattt   1500
tacaaaatgg agagtcatcc ctacctcaaa ttactgacga tgtaatggga agggattttg   1560
atgatgttgg ccaagaagat gcaaatgatg ttccaatgct tgatgaagaa gaaatggttg   1620
attctgaatc tgaatgctct gatgatgaac ctgacctaga aaccacttca gatgatgatc   1680
cagaaattgt tgatgtcagc aaggttttgc tagggataaa gggatctcat gtgaaataca   1740
aggatctgtg ggttgtcttt gatcctgagc agcggagtta cttggagtca cgattgcgga   1800
gatacaggaa ggttgtgggt ccagcgctat ccgagagaat ggtccattcg ctcggataat   1860
gttaatgttg gtacttgaat ttaataagat gctactgtta atctccccag gaaaaaaaa    1920
aaaaaaactc tgcaaagaag attcatgtat tcttcctttg aatggtctga caatgttggc   1980
aatagcaatg ttgtgaaccc ataagttttt ggttaatgga catttacat atctttttt     2040
acaaaaaaa aaaaaaaaa                                                  2060
```

<210> SEQ ID NO 2
<211> LENGTH: 611
<212> TYPE: PRT
<213> ORGANISM: Glycine max

<400> SEQUENCE: 2

Met Ala Ser Ser Ser Ser Asn Thr Pro Lys Glu Ser Val Val Asp Asp

-continued

```
  1               5               10              15
Arg Gly Arg Arg Arg Thr Ser Cys Gly Tyr Cys Arg Ser Ser Arg Asp
                20              25              30
Asn Ser Ile Ser His Gly Met Trp Ala His Ser Leu Thr Val Asp Asp
            35              40              45
Tyr Gln Asp Leu Leu Asp Cys Gly Trp Arg Arg Ser Gly Cys Phe Leu
        50              55              60
Tyr Lys Pro Glu Met Glu Arg Thr Cys Cys Pro Ser Tyr Thr Ile Arg
 65             70              75              80
Leu Lys Ala Ser Asn Phe Val Pro Ser Lys Glu Gln Leu Arg Val Ser
                85              90              95
Ile Arg Met Gln Arg Phe Leu Asp Gly Thr Leu Asp Val Lys Lys Val
               100             105             110
Asp Val Thr Glu Asp Pro Thr Lys Ser Gly Asn Phe Ser Ser Pro Met
            115             120             125
Ser Glu Glu Ser Leu Ala Ala Gly Ser Glu Asn Lys Asp Glu Val Glu
        130             135             140
Lys Ser Leu His Leu Ser Asn Gln Ile Asp Asn Val Ile His Ile Leu
145             150             155             160
Ile Glu Arg Gly Glu Phe Ala Ser Gly Ile Gln Leu Pro Lys Ala Ser
                165             170             175
Val Lys Arg Val Ser Gln Gly Lys Arg Lys Leu Leu Val Asn Gly Ser
            180             185             190
Glu Asp Leu Leu Tyr Ser Ser Asn Ile Ala Phe Gln Ile Ala Ala Ser
        195             200             205
Ile Lys Arg Ala Gln Ser Cys Asp Lys Val Val Asn Asp Ser Lys Pro
210             215             220
Ser Arg Val Cys Glu Lys Glu Asn Asp Ser Ser Pro Lys Ile Ile Ala
225             230             235             240
Glu Lys Leu Val Ala Ser Leu Asp Pro Thr Val Lys Asn Ser Gly Leu
            245             250             255
Ser Ile Arg Ala Cys Asn Gly His Ile Asn Phe Tyr Ala Ser Ser Lys
                260             265             270
Gln Val Ser Leu Asn Arg Ser Val Gln Asn Ala Pro Val Pro Lys Asn
            275             280             285
Ser Arg Met Lys His Tyr Ser Gly Gly Asn Cys Leu Ile Gly Gln Val
        290             295             300
Lys Arg Arg Lys Leu Glu Ile Arg Leu Asn Arg Ser Ser Phe Asp Pro
305             310             315             320
Glu Glu Phe Ala Leu Tyr Arg Arg Tyr Gln Leu Lys Val His Asn Asp
            325             330             335
Lys Pro Gln Asn Val Thr Glu Asn Ser Tyr Arg Ser Phe Leu Val Asp
        340             345             350
Thr Pro Leu Ile Gln Val Ser Pro Thr Gly Gly Ser Thr Val Pro Pro
        355             360             365
Cys Gly Phe Gly Ser Phe His Gln Gln Tyr Leu Ile Asp Gly Gln Leu
        370             375             380
Val Ala Val Gly Val Ile Asp Ile Leu Pro Lys Cys Leu Ser Ser Lys
385             390             395             400
Tyr Leu Phe Trp Asp Pro Asp Phe Ala Tyr Leu Ser Leu Gly Lys Tyr
                405             410             415
Ser Ala Phe Gln Glu Ile Gly Trp Val Lys Glu Asn Gln Val Tyr Cys
            420             425             430
```

| | | | | | | | | | | | | |
|---|---|---|---|---|---|---|---|---|---|---|---|---|
|Pro|Ser|Leu|Gln|Tyr|Tyr|Leu|Gly|Tyr|Tyr|Ile|His|Ser|Cys|Asn|
| | |435| | | |440| | | |445| | | | |

Pro Ser Leu Gln Tyr Tyr Leu Gly Tyr Tyr Ile His Ser Cys Asn
        435             440             445

Lys Met Arg Tyr Lys Ala Ala Tyr His Pro Ser Glu Leu Leu Cys Pro
    450             455             460

Leu Arg Tyr Gln Trp Val Pro Phe Asp Ile Ala Arg Pro Leu Leu Asp
465             470             475             480

Arg Lys Pro Tyr Val Val Leu Ser Asp Ser Ser Ile Leu Gln Asn Gly
            485             490             495

Glu Ser Ser Leu Pro Gln Ile Thr Asp Asp Val Met Gly Arg Asp Phe
        500             505             510

Asp Asp Val Gly Gln Glu Asp Ala Asn Asp Val Pro Met Leu Asp Glu
        515             520             525

Glu Glu Met Val Asp Ser Glu Ser Glu Cys Ser Asp Asp Glu Pro Asp
        530             535             540

Leu Glu Thr Thr Ser Asp Asp Pro Glu Ile Val Asp Val Ser Lys
545             550             555             560

Val Leu Leu Gly Ile Lys Gly Ser His Val Lys Tyr Lys Asp Leu Trp
            565             570             575

Val Val Phe Asp Pro Glu Gln Arg Ser Tyr Leu Glu Ser Arg Leu Arg
        580             585             590

Arg Tyr Arg Lys Val Val Gly Pro Ala Leu Ser Glu Arg Met Val His
        595             600             605

Ser Leu Gly
    610

<210> SEQ ID NO 3
<211> LENGTH: 1954
<212> TYPE: DNA
<213> ORGANISM: Triticum aestivum

<400> SEQUENCE: 3

```
gcacgagaag ctcttcttga ccgtggatgg aggaggtctg gctgtttct  ctacaagcct      60
gagatggaac ggacatgctg tccggcatat actatacgtc tgaaggcaag tgatttcatt     120
tgttccaaag agcaagaccg tgtacttaaa aggatgcaaa ggtttcttga tggagagctt     180
gacccacagg ttggaagtcc acagtgcaag actaaccta caaaacgttc actcaatgaa     240
cctatgaatt caccaacctt gaaagtatcc agggtatcag catatgaatt tcaaacagcc     300
acgggtccaa gtttagacaa agaagatgag tttattagtt tcctgtctag caaaatcaat     360
gaggcaatag gtacgtgctt ccaaggtgga atagtaggtt ctgatgttga actccctaaa     420
gctgttgtga agactgttaa acctcaagta aaaaagaaag taggaggagc agcacaagaa     480
aagaaaggag gagcagtgca agatttggtg tactcatgca atgtaagttt ccaactggct     540
gcagtaatta acgtgcatt gcctgaagaa aaatgtgcag tattagggga cctttctcca     600
aactgtattg cagaaaggct ggtgttgaca atggagcatc atggagaaat agctggtttt     660
gcagtgaaag cctgtaatgg ccatctgaac ttctattcag ccactattca gccaattcag     720
aatcatacta gcattgatgc atctgcacaa gcttcttcag ataggtcgac tagctcaaaa     780
caaagctctg tgaacaaaaa tgatgcaaga cataataaaa aagcaagaaa gctggaattt     840
aagatggcaa aatcacattt tgaccctgag gagtttgctt tgtaccaaag atatcagaca     900
aaagttcaca aggaaaagac agttacgaaa agctcataca agagatttct ggtcgatacc     960
ccaattgtac ctattccccc aaggagtggt gataatacag ttccgccatg cggttttggt    1020
```

-continued

```
tcatttcatc agcagtatag aattgatgga aaacttgtgg cagttggtgt agttgatatc      1080
cttcctaaat gtctctcaag caaatatttg ttctgggatc ctgaccttgc tttcctatct      1140
cttggaaagt atacagctct aaaggaaata gattgggtca agacaacaca gaaaagttgc      1200
cccagccttg agtactatta ccttggttat tatatacatt cctgcaacaa gatgagatac      1260
aaagctgcat atcgaccatc agaacttctc tgtccagtcc gttatgagtg ggtgcgctat      1320
gatgctgcaa aaccccttact agataagagc ctgtattctg ttatatctga tttctccacc      1380
atggcgcaag atgaaatccc ccaaccacac gcttgtggtc cttgtgatgg atcttcagca      1440
caaaacgacc acagtgagac tcctattgat gaggatgatg aggactcaga gtcagactat      1500
gatgaatcag acatgatggt tgatgaagag atggttcatt cagagtctaa aggtgataca      1560
gctgaggaat gttccgacgt agatgttgaa aacgttatca tgggcctgag cggctctcgg      1620
gttaaataca aggaacttca cagcgttgtc gggccaatcg acaggagaca cctgagtgag      1680
ctggaaaggc agctgagcag atacgcgaaa gtcgttggga aggagctgtc tgaccgtatc      1740
gtctattccc ttagctgagc agcaaacatt ctgcatggca aacgcaacac agccgtccga      1800
aactcgtctc cgattgtttg tgcaagtcat gtaggaaacc agaaactcct ctccgattgt      1860
ttgtgcaagt catgtaggaa acgagatata gatggctgga aaccgatgat gctttcatta      1920
tcaatcgatt cataaaaaaa aaaaaaaaaa aaaa                                  1954
```

<210> SEQ ID NO 4
<211> LENGTH: 585
<212> TYPE: PRT
<213> ORGANISM: Triticum aestivum

<400> SEQUENCE: 4

```
Ala Arg Glu Ala Leu Leu Asp Arg Gly Trp Arg Arg Ser Gly Cys Phe
  1               5                  10                  15

Leu Tyr Lys Pro Glu Met Glu Arg Thr Cys Cys Pro Ala Tyr Thr Ile
                 20                  25                  30

Arg Leu Lys Ala Ser Asp Phe Ile Cys Ser Lys Glu Gln Asp Arg Val
             35                  40                  45

Leu Lys Arg Met Gln Arg Phe Leu Asp Gly Glu Leu Asp Pro Gln Val
         50                  55                  60

Gly Ser Pro Gln Cys Lys Thr Asn Pro Thr Lys Arg Ser Leu Asn Glu
 65                  70                  75                  80

Pro Met Asn Ser Pro Thr Leu Lys Val Ser Arg Val Ser Ala Tyr Glu
                 85                  90                  95

Phe Gln Thr Ala Thr Gly Pro Ser Leu Asp Lys Glu Asp Glu Phe Ile
                100                 105                 110

Ser Phe Leu Ser Ser Lys Ile Asn Glu Ala Ile Gly Thr Cys Phe Gln
            115                 120                 125

Gly Gly Ile Val Gly Ser Asp Val Glu Leu Pro Lys Ala Val Val Lys
        130                 135                 140

Thr Val Lys Pro Gln Val Lys Lys Val Gly Gly Ala Ala Gln Glu
145                 150                 155                 160

Lys Lys Gly Gly Ala Val Gln Asp Leu Val Tyr Ser Cys Asn Val Ser
                165                 170                 175

Phe Gln Leu Ala Ala Val Ile Lys Arg Ala Leu Pro Glu Glu Lys Cys
            180                 185                 190

Ala Val Leu Gly Asp Leu Ser Pro Asn Cys Ile Ala Glu Arg Leu Val
        195                 200                 205
```

-continued

Leu Thr Met Glu His His Gly Glu Ile Ala Gly Phe Ala Val Lys Ala
           210                 215                 220

Cys Asn Gly His Leu Asn Phe Tyr Ser Ala Thr Ile Gln Pro Ile Gln
225                 230                 235                 240

Asn His Thr Ser Ile Asp Ala Ser Ala Gln Ala Ser Ser Asp Arg Ser
                245                 250                 255

Thr Ser Ser Lys Gln Ser Ser Val Asn Lys Asn Asp Ala Arg His Asn
            260                 265                 270

Lys Lys Ala Arg Lys Leu Glu Phe Lys Met Ala Lys Ser His Phe Asp
        275                 280                 285

Pro Glu Glu Phe Ala Leu Tyr Gln Arg Tyr Gln Thr Lys Val His Lys
    290                 295                 300

Glu Lys Thr Val Thr Glu Ser Ser Tyr Lys Arg Phe Leu Val Asp Thr
305                 310                 315                 320

Pro Ile Val Pro Ile Pro Pro Arg Ser Gly Asp Asn Thr Val Pro Pro
                325                 330                 335

Cys Gly Phe Gly Ser Phe His Gln Gln Tyr Arg Ile Asp Gly Lys Leu
            340                 345                 350

Val Ala Val Gly Val Val Asp Ile Leu Pro Lys Cys Leu Ser Ser Lys
        355                 360                 365

Tyr Leu Phe Trp Asp Pro Asp Leu Ala Phe Leu Ser Leu Gly Lys Tyr
    370                 375                 380

Thr Ala Leu Lys Glu Ile Asp Trp Val Lys Thr Thr Gln Lys Ser Cys
385                 390                 395                 400

Pro Ser Leu Glu Tyr Tyr Leu Gly Tyr Tyr Ile His Ser Cys Asn
                405                 410                 415

Lys Met Arg Tyr Lys Ala Ala Tyr Arg Pro Ser Glu Leu Leu Cys Pro
            420                 425                 430

Val Arg Tyr Glu Trp Val Arg Tyr Asp Ala Ala Lys Pro Leu Leu Asp
        435                 440                 445

Lys Ser Leu Tyr Ser Val Ile Ser Asp Phe Ser Thr Met Ala Gln Asp
    450                 455                 460

Glu Ile Pro Gln Pro His Ala Cys Gly Pro Cys Asp Gly Ser Ser Ala
465                 470                 475                 480

Gln Asn Asp His Ser Glu Thr Pro Ile Asp Glu Asp Asp Glu Asp Ser
                485                 490                 495

Glu Ser Asp Tyr Asp Glu Ser Asp Met Met Val Asp Glu Met Val
            500                 505                 510

His Ser Glu Ser Lys Gly Asp Thr Ala Glu Glu Cys Ser Asp Val Asp
        515                 520                 525

Val Glu Asn Val Ile Met Gly Leu Ser Gly Ser Arg Val Lys Tyr Lys
    530                 535                 540

Glu Leu His Ser Val Val Gly Pro Ile Asp Arg Arg His Leu Ser Glu
545                 550                 555                 560

Leu Glu Arg Gln Leu Ser Arg Tyr Ala Lys Val Val Gly Lys Glu Leu
                565                 570                 575

Ser Asp Arg Ile Val Tyr Ser Leu Ser
            580                 585

<210> SEQ ID NO 5
<211> LENGTH: 2636
<212> TYPE: DNA
<213> ORGANISM: Zea mays

<400> SEQUENCE: 5

-continued

```
gcacgagaaa ccctagacgc caccctcccc cgccgcgcgc cgccgcccgc ggacatggat      60
ctccttcgct ctcatctcca caaggtccgg atccccgagc caaccaaccg catccacaag     120
gacgagtgct gcgtctcctt cgacactccg aggtcagagg gaggcctgta cgtggacatg     180
gtctcgttcc tggggttcgg gagggagtac gtggagtgga acttcgagaa gacgggaac      240
cccgtgtacc tccacatcgt tcagcgccgg aagccggagc ccgacgaggc ggatcgcccg     300
cttaagaagc ccaccctcct cgctataggt gtggaaggag gttttggtga tcaagaacca     360
gaatatgatg aaacttttga aatagtcatc ttacctgatt ttatttgtct tccatttccg     420
tcagttgatt tgccagagaa ggttaggctt gcggttgata agttttact tgctgaaagt      480
gctgatagaa aagaacaact ggctgcttgg gttgctgaca aaagaacat tagtgcatat      540
gctatggacc tgcagcagct agacaatggt gttattgtgc ctcctactgg atggaagtgt     600
agcaaatgcg ataaaactga gaacctctgg ctgaatttaa ctgatggtat gatcctttgt     660
gggaggaagc tctgggatgg aagtggtggg aataatcatg ccattgaaca ttatgaacag     720
actaaatacc ctcttgcggt gaagcttgga acaattactg ctgatttgga agcggcagat     780
gttttctcgt accctgaaga tgatagtgtt gaagatccgc tattagctca gcacttatca     840
cattttggta tcgattttc ttcactccaa aagactgaga tgactactgc tgagagggaa      900
cttgatgcta acacaaatta tgactggaat agaatacaag aaagtggaaa agacgctgag     960
cttctgtttg gacccggcta tactggtctt gcgaatcttg ggaatagttg ctatatggct    1020
tcaataatgc aagtcatgtt ttcaatccat cctttcatat caaggtactt cgagaaacag    1080
agtttgaaag ctgcatttgc aactgcaccc gctgatccaa cagtagacct aaacatgcaa    1140
ctgacaaaac tagcgcatgg tttgctctct ggtaaatatt ctgctccagc aaaggagggg    1200
caagaaggga tacgttctcg catgtttaag tcagttatca ctgcgaacca tcctgaattt    1260
tcaagcatga dacaacagga tgtccttgaa ttcttccttc accttattga cagagttgag    1320
aaggcaaacc ctgagaccg tgagctaaat cctttttccg gtttcaagtt tgttgttgaa    1380
gagagggttc agtgcccttc tgggaaggtt tcttacaaca aacgatctga caacgttctt    1440
tctttgagca taccactgca tgaggcaact aataaagagc agctagaagc ttttaatgag    1500
aagaaagctg caatgaactt ggatggaaaa gaagtgtcta atgaggatat tgtcaggcct    1560
agagtcccat tggaggcatg cttgtcaagt ttttcagggc cagaggagat tccagatttt    1620
tatagcactg cattaaattc aaagactacc gtcactaaga cagctggttt cactacccttt   1680
cctgattacc ttgtgctgca catgcgtaag tttgtaatgg aaacaggatg ggtgccaaag    1740
aaactcgatg tttatataga tgtgccagat acaattgata tcacacatat gcgcagcaaa    1800
ggattacagc ctggggaaga gctgctacct gaaggaggtt ctggtgacga cagtgccgag    1860
cctgctaatc ctgttgccag tgaggatatt gtaacccagc ttgcaagcat gggcttcaac    1920
taccttcatt gtcagaaagc tgctattaac acatcaaaca caggagttga ggaagcgatg    1980
aattggctcc tctcgcacat ggatgatcca gatataaacg acccaatatc aaaagattca    2040
cgtgcttatg agccatctgt tgacgaagca agtgttcaaa ctctcatctc ctttggattc    2100
caggaagaca ttgccataaa ggccctgaaa gcttctggtg gtaatatcga gaaagctaca    2160
gactggattt tcagccaccc cgaagcatct acctcagcat ctgctgattc ttccactagc    2220
aatgtaaatg ctgatgacac atatattcca gatggaagtg gcagatacaa gctgatggcg    2280
ttcgtgagcc atatgggcac ctctacccac tgcgggcact acgtagctca tgtcctcaaa    2340
```

-continued

```
gacgggaggt ggacaatctt taacgacagc aaggtcgcag tatctgttga cctgcccaag    2400
gaaatgggct acctctattt ctttcagagg attagcaact aggcacgtca cacaatggaa    2460
agaatggtgg gctgttagga tactgtcttg ctgattttaa agcgaacgtt tactcacatc    2520
ctgccatgct ggttactgaa tggtcaaccg ggatatttgc tttttgttc cttgagacct     2580 cgattggcat cttccggtta catctgtgtt tttttatta aaaaaaaaaa aaaaaa         2636
```

<210> SEQ ID NO 6
<211> LENGTH: 795
<212> TYPE: PRT
<213> ORGANISM: Zea mays

<400> SEQUENCE: 6

```
Met Asp Leu Leu Arg Ser His Leu His Lys Val Arg Ile Pro Glu Pro
 1               5                  10                  15

Thr Asn Arg Ile His Lys Asp Glu Cys Cys Val Ser Phe Asp Thr Pro
             20                  25                  30

Arg Ser Glu Gly Gly Leu Tyr Val Asp Met Val Ser Phe Leu Gly Phe
         35                  40                  45

Gly Arg Glu Tyr Val Glu Trp Asn Phe Glu Lys Thr Gly Asn Pro Val
     50                  55                  60

Tyr Leu His Ile Val Gln Arg Arg Lys Pro Glu Pro Asp Glu Ala Asp
 65                  70                  75                  80

Arg Pro Leu Lys Lys Pro Thr Leu Leu Ala Ile Gly Val Glu Gly Gly
                 85                  90                  95

Phe Gly Asp Gln Glu Pro Glu Tyr Asp Glu Thr Phe Glu Ile Val Ile
            100                 105                 110

Leu Pro Asp Phe Ile Cys Leu Pro Phe Pro Ser Val Asp Leu Pro Glu
        115                 120                 125

Lys Val Arg Leu Ala Val Asp Lys Val Leu Leu Ala Glu Ser Ala Asp
    130                 135                 140

Arg Lys Glu Gln Leu Ala Ala Trp Val Ala Asp Lys Lys Asn Ile Ser
145                 150                 155                 160

Ala Tyr Ala Met Asp Leu Gln Gln Leu Asp Asn Gly Val Ile Val Pro
                165                 170                 175

Pro Thr Gly Trp Lys Cys Ser Lys Cys Asp Lys Thr Glu Asn Leu Trp
            180                 185                 190

Leu Asn Leu Thr Asp Gly Met Ile Leu Cys Gly Arg Lys Leu Trp Asp
        195                 200                 205

Gly Ser Gly Gly Asn Asn His Ala Ile Glu His Tyr Glu Gln Thr Lys
    210                 215                 220

Tyr Pro Leu Ala Val Lys Leu Gly Thr Ile Thr Ala Asp Leu Glu Ala
225                 230                 235                 240

Ala Asp Val Phe Ser Tyr Pro Glu Asp Ser Val Glu Asp Pro Leu
                245                 250                 255

Leu Ala Gln His Leu Ser His Phe Gly Ile Asp Phe Ser Ser Leu Gln
            260                 265                 270

Lys Thr Glu Met Thr Thr Ala Glu Arg Glu Leu Asp Ala Asn Thr Asn
        275                 280                 285

Tyr Asp Trp Asn Arg Ile Gln Glu Ser Gly Lys Asp Ala Glu Leu Leu
    290                 295                 300

Phe Gly Pro Gly Tyr Thr Gly Leu Ala Asn Leu Gly Asn Ser Cys Tyr
305                 310                 315                 320

Met Ala Ser Ile Met Gln Val Met Phe Ser Ile His Pro Phe Ile Ser
```

```
                    325                 330                 335
Arg Tyr Phe Glu Lys Gln Ser Leu Lys Ala Ala Phe Ala Thr Ala Pro
                340                 345                 350
Ala Asp Pro Thr Val Asp Leu Asn Met Gln Leu Thr Lys Leu Ala His
                355                 360                 365
Gly Leu Leu Ser Gly Lys Tyr Ser Ala Pro Ala Lys Glu Gly Gln Glu
                370                 375                 380
Gly Ile Arg Ser Arg Met Phe Lys Ser Val Ile Thr Ala Asn His Pro
385                 390                 395                 400
Glu Phe Ser Ser Met Arg Gln Gln Asp Val Leu Glu Phe Phe Leu His
                    405                 410                 415
Leu Ile Asp Arg Val Glu Lys Ala Asn Pro Gly Asp Arg Glu Leu Asn
                420                 425                 430
Pro Phe Ser Gly Phe Lys Phe Val Glu Glu Arg Val Gln Cys Pro
                435                 440                 445
Ser Gly Lys Val Ser Tyr Asn Lys Arg Ser Asp Asn Val Leu Ser Leu
                450                 455                 460
Ser Ile Pro Leu His Glu Ala Thr Asn Lys Glu Gln Leu Glu Ala Phe
465                 470                 475                 480
Asn Glu Lys Lys Ala Ala Met Asn Leu Asp Gly Lys Glu Val Ser Asn
                    485                 490                 495
Glu Asp Ile Val Arg Pro Arg Val Pro Leu Glu Ala Cys Leu Ser Ser
                500                 505                 510
Phe Ser Gly Pro Glu Glu Ile Pro Asp Phe Tyr Ser Thr Ala Leu Asn
                515                 520                 525
Ser Lys Thr Thr Val Thr Lys Thr Ala Gly Phe Thr Thr Phe Pro Asp
                530                 535                 540
Tyr Leu Val Leu His Met Arg Lys Phe Val Met Glu Thr Gly Trp Val
545                 550                 555                 560
Pro Lys Lys Leu Asp Val Tyr Ile Asp Val Pro Asp Thr Ile Asp Ile
                    565                 570                 575
Thr His Met Arg Ser Lys Gly Leu Gln Pro Gly Glu Glu Leu Leu Pro
                580                 585                 590
Glu Gly Gly Ser Gly Asp Asp Ser Ala Glu Pro Ala Asn Pro Val Ala
                595                 600                 605
Ser Glu Asp Ile Val Thr Gln Leu Ala Ser Met Gly Phe Asn Tyr Leu
                610                 615                 620
His Cys Gln Lys Ala Ala Ile Asn Thr Ser Asn Thr Gly Val Glu Glu
625                 630                 635                 640
Ala Met Asn Trp Leu Leu Ser His Met Asp Asp Pro Asp Ile Asn Asp
                    645                 650                 655
Pro Ile Ser Lys Asp Ser Arg Ala Tyr Glu Pro Ser Val Asp Glu Ala
                660                 665                 670
Ser Val Gln Thr Leu Ile Ser Phe Gly Phe Gln Glu Asp Ile Ala Ile
                675                 680                 685
Lys Ala Leu Lys Ala Ser Gly Gly Asn Ile Glu Lys Ala Thr Asp Trp
                690                 695                 700
Ile Phe Ser His Pro Glu Ala Ser Thr Ser Ala Ser Ala Asp Ser Ser
705                 710                 715                 720
Thr Ser Asn Val Asn Ala Asp Asp Thr Tyr Ile Pro Asp Gly Ser Gly
                    725                 730                 735
Arg Tyr Lys Leu Met Ala Phe Val Ser His Met Gly Thr Ser Thr His
                740                 745                 750
```

```
Cys Gly His Tyr Val Ala His Val Leu Lys Asp Gly Arg Trp Thr Ile
        755                 760                 765

Phe Asn Asp Ser Lys Val Ala Val Ser Val Asp Leu Pro Lys Glu Met
    770                 775                 780

Gly Tyr Leu Tyr Phe Phe Gln Arg Ile Ser Asn
785                 790                 795

<210> SEQ ID NO 7
<211> LENGTH: 2407
<212> TYPE: DNA
<213> ORGANISM: Oryza sativa

<400> SEQUENCE: 7
gcacgaggct tggaacaatt actgctgatt tagaagcagc agacgttttc tcatacccag      60
aagatgatag cgttgaagat ccactattag cgcagcattt gtcacatttt ggtattgatt     120
tttcttcact ccaaaagacc gagatgacta ctgctgaaag agagcttgat cacaacacaa     180
attatgactg gaatagaata caagaaagtg gcaaagatgc cgaacttttta tacggccctg     240 gttatactgg ccttgtaaat cttggaaata gttgctatat ggcctcagta atgcaagtta     300
tgttttcaac tcatccttt atatcacgct actttgagaa gcagagcttg aaagctgcat      360
ttgcaattgc cccagctgat ccaacattgg acttgaacat gcaaatgaca agttggctc      420 atggaatgct ctctggcaaa tactctgtgc caaatcagga gggacaagaa ggaatacacc      480
ctcgtatgtt aagacagtt attgctgcaa agcatcccga attttccagt atgaggcaac      540
aggatgcgct tgatttcttc cttcatctta ttgaccaagt tgatcaggca acaccggaa      600 accatgagct gaatcctttt acagggttca aattcttcat tgaggagcgt cttcaatgcc      660
cttctggaaa agtctcctat aacaaacgtt ctgactacat tctttctttg aacataccgt      720
tacatgaagc tactaacaaa gagcagctag aagcatttca tgaagaaaa gctgcaatgg      780 atttggatgg aaaggaagtg tctaatgagg aaattgtgag gcctagagtc ccactggagg      840
catgcttagc aagttttca ggcgcggagg aagtgcctga attttacagc actgcattga     900
attcaaagac aacagcaatt aagactgctg ctttaaaac atttcctgat tacctggtgt      960
tgcagatgcg caagtttgta atggaagcag atgggtgcc aaagaaacta gatgtatacg     1020
tagatgtgcc agatataatt gatatctcgc acatgcgcag caaaggcata cagcctggtg     1080
aagagctact acctgaagga gcttctggtg ataacaaagc tgaacctgtt catcctgttg     1140
ccagtgagga cattgtatct cagctggcaa gcatgggtt caattatctt cattgccaga     1200
aagctgctat tagtacatca aacacaggag ttgaggaggc gatgaattgg cttctctcac     1260
acatggatga tccagatatc aacgatccaa tatctaaaga ttcacaggct gctgaacaaa     1320
ctgttgatga aactagcgtt caaactcttg tttccttcgg atttcaagaa gatgttgctc     1380
gaaaggcctt ggcagcttct ggtggaaata tcgagagagc aacagactgg attttagcc     1440 accctgaggc ttttagctca gtacctactg attcttcaac aagcaatatg gaagatgatg     1500
atgcacacat accagatgga agtggcagat acaaattgat ggcgtttgtg agccatatgg     1560
gcacctctac ccattgtggg cactacgttc cccatgtcct caaagacggg aggtgggtaa     1620
tattcaatga tagtaaggtt gctgcctctg tcgacttgcc caaggatatg ggatacctgt     1680
atttctttca aaggatataa agcattagca gctgaaagac ttcacaggca agaaatacat     1740
tcgctcgctg acttgagtct tagttatggg cacctatgat caaaagcacg gcggatagtc     1800
ggtgaacttg catgcagatg gacttagagc gagtgttggt cacatcctgt cgtgctgact     1860
```

-continued

```
ttagactgat cgatcagctg ggatatcact tgttccatg gcattatgca ttggcacatt   1920
caattcttct tgtcgatct atcatcttag cgttaacatt ctgccatgaa aaaaaaaaa    1980 aaaaaaaaaa aaaaaaaaaa aaaaaaaaaa aaaaaaaaaa aaaaaaaaaa aaaaaaaaaa  2040
aaaaactccg gggggggcc cggaaccaaa ttcccccaaa attaattcta ataacccccc    2100
caaattggcc ttcttttaaa aacttcttgt gggaaaaacc ttgggtttac caaattaaat   2160
ccctttgaaa aaatcccct tttcccaaat tgggtaaaaa aaaaaaaggc ccaaaccatt    2220
tccctttcca aaaattttcc aaacctaaat ggcaaatgga accccccctt taccgggcaa   2280
taaaaccggg ggggtttggt gtttaaccca aagttaaccg ctaaaatttc aaaccccaa    2340 acgcccgccc ctttccattt ttttcctttc tttttcacaa aattttcccg agttttcccc   2400
ttaaaat                                                             2407
```

<210> SEQ ID NO 8
<211> LENGTH: 565
<212> TYPE: PRT
<213> ORGANISM: Oryza sativa

<400> SEQUENCE: 8

```
Thr Arg Leu Gly Thr Ile Thr Ala Asp Leu Glu Ala Ala Asp Val Phe
 1               5                  10                  15

Ser Tyr Pro Glu Asp Asp Ser Val Glu Asp Pro Leu Leu Ala Gln His
                20                  25                  30

Leu Ser His Phe Gly Ile Asp Phe Ser Ser Leu Gln Lys Thr Glu Met
            35                  40                  45

Thr Thr Ala Glu Arg Glu Leu Asp His Asn Thr Asn Tyr Asp Trp Asn
        50                  55                  60

Arg Ile Gln Glu Ser Gly Lys Asp Ala Glu Leu Leu Tyr Gly Pro Gly
    65                  70                  75                  80

Tyr Thr Gly Leu Val Asn Leu Gly Asn Ser Cys Tyr Met Ala Ser Val
                85                  90                  95

Met Gln Val Met Phe Ser Thr His Pro Phe Ile Ser Arg Tyr Phe Glu
            100                 105                 110

Lys Gln Ser Leu Lys Ala Ala Phe Ala Ile Ala Pro Ala Asp Pro Thr
        115                 120                 125

Leu Asp Leu Asn Met Gln Met Thr Lys Leu Ala His Gly Met Leu Ser
    130                 135                 140

Gly Lys Tyr Ser Val Pro Asn Gln Glu Gly Gln Gly Ile His Pro
145                 150                 155                 160

Arg Met Phe Lys Thr Val Ile Ala Ala Lys His Pro Glu Phe Ser Ser
                165                 170                 175

Met Arg Gln Gln Asp Ala Leu Asp Phe Phe Leu His Leu Ile Asp Gln
            180                 185                 190

Val Asp Gln Ala Asn Thr Gly Asn His Glu Leu Asn Pro Phe Thr Gly
        195                 200                 205

Phe Lys Phe Phe Ile Glu Glu Arg Leu Gln Cys Pro Ser Gly Lys Val
    210                 215                 220

Ser Tyr Asn Lys Arg Ser Asp Tyr Ile Leu Ser Leu Asn Ile Pro Leu
225                 230                 235                 240

His Glu Ala Thr Asn Lys Glu Gln Leu Glu Ala Phe His Glu Lys Lys
                245                 250                 255

Ala Ala Met Asp Leu Asp Gly Lys Glu Val Ser Asn Glu Glu Ile Val
            260                 265                 270
```

-continued

```
Arg Pro Arg Val Pro Leu Glu Ala Cys Leu Ala Ser Phe Ser Gly Ala
        275                 280                 285

Glu Glu Val Pro Glu Phe Tyr Ser Thr Ala Leu Asn Ser Lys Thr Thr
290                 295                 300

Ala Ile Lys Thr Ala Gly Phe Lys Thr Phe Pro Asp Tyr Leu Val Leu
305                 310                 315                 320

Gln Met Arg Lys Phe Val Met Glu Ala Gly Trp Val Pro Lys Lys Leu
                325                 330                 335

Asp Val Tyr Val Asp Val Pro Asp Ile Ile Asp Ile Ser His Met Arg
            340                 345                 350

Ser Lys Gly Ile Gln Pro Gly Glu Glu Leu Leu Pro Glu Gly Ala Ser
        355                 360                 365

Gly Asp Asn Lys Ala Glu Pro Val His Pro Val Ala Ser Glu Asp Ile
370                 375                 380

Val Ser Gln Leu Ala Ser Met Gly Phe Asn Tyr Leu His Cys Gln Lys
385                 390                 395                 400

Ala Ala Ile Ser Thr Ser Asn Thr Gly Val Glu Glu Ala Met Asn Trp
                405                 410                 415

Leu Leu Ser His Met Asp Asp Pro Asp Ile Asn Asp Pro Ile Ser Lys
            420                 425                 430

Asp Ser Gln Ala Ala Glu Gln Thr Val Asp Glu Thr Ser Val Gln Thr
        435                 440                 445

Leu Val Ser Phe Gly Phe Gln Glu Asp Val Ala Arg Lys Ala Leu Ala
    450                 455                 460

Ala Ser Gly Gly Asn Ile Glu Arg Ala Thr Asp Trp Ile Phe Ser His
465                 470                 475                 480

Pro Glu Ala Phe Ser Ser Val Pro Thr Asp Ser Ser Thr Ser Asn Met
                485                 490                 495

Glu Asp Asp Ala His Ile Pro Asp Gly Ser Gly Arg Tyr Lys Leu
            500                 505                 510

Met Ala Phe Val Ser His Met Gly Thr Ser Thr His Cys Gly His Tyr
        515                 520                 525

Val Ala His Val Leu Lys Asp Gly Arg Trp Val Ile Phe Asn Asp Ser
530                 535                 540

Lys Val Ala Ala Ser Val Asp Leu Pro Lys Asp Met Gly Tyr Leu Tyr
545                 550                 555                 560

Phe Phe Gln Arg Ile
                565

<210> SEQ ID NO 9
<211> LENGTH: 578
<212> TYPE: DNA
<213> ORGANISM: Zea mays
<220> FEATURE:
<221> NAME/KEY: unsure
<222> LOCATION: (47)

<400> SEQUENCE: 9
gtttatatag atgtgccaga tacaattgat atcacacata tgcgcanaaa ggattacagc      60
ctggggaaga gctgctacct gaaggaggtt ctggtgacga cagtgccgag cctgctaatc    120
ctgttgccag tgaggatatt gtaacccagc ttgcaagcat gggcttcaac taccttcatt    180
gtcagaaagc tgctattaac acatcaaaca caggagttga ggaagcgatg aattggctcc    240
tctcgcacat ggatgatcca gatataaacg acccaatatc aaaagattca cgtgcttatg    300
```

```
agccatctgt tgacgaagca agtgttcaaa ctctcatctc ctttggattc caggaagaca    360
ttgccataaa ggccctgaaa gcttctggtg gtaatatcga gaaagctaca gactggattt    420
tcagccaccc cgaagcatct acctcagcat ctgctgattc ttccactagc aatgtaaatg    480
ctgatgacac atatattcca gatggaagtg gcagatacaa gctgatggcg ttcgtgagcc    540
atatgggcac ctctaaccca ctgcgggcac tacgtagc                            578
```

```
<210> SEQ ID NO 10
<211> LENGTH: 192
<212> TYPE: PRT
<213> ORGANISM: Zea mays
<220> FEATURE:
<221> NAME/KEY: UNSURE
<222> LOCATION: (16)..(17)

<400> SEQUENCE: 10
```

Val Tyr Ile Asp Val Pro Asp Thr Ile Asp Ile Thr His Met Arg Xaa
 1               5                  10                  15

Xaa Gly Leu Gln Pro Gly Glu Glu Leu Leu Pro Glu Gly Gly Ser Gly
            20                  25                  30

Asp Asp Ser Ala Glu Pro Ala Asn Pro Val Ala Ser Glu Asp Ile Val
        35                  40                  45

Thr Gln Leu Ala Ser Met Gly Phe Asn Tyr Leu His Cys Gln Lys Ala
    50                  55                  60

Ala Ile Asn Thr Ser Asn Thr Gly Val Glu Glu Ala Met Asn Trp Leu
65                  70                  75                  80

Leu Ser His Met Asp Asp Pro Asp Ile Asn Asp Pro Ile Ser Lys Asp
                85                  90                  95

Ser Arg Ala Tyr Glu Pro Ser Val Asp Glu Ala Ser Val Gln Thr Leu
            100                 105                 110

Ile Ser Phe Gly Phe Gln Glu Asp Ile Ala Ile Lys Ala Leu Lys Ala
        115                 120                 125

Ser Gly Gly Asn Ile Glu Lys Ala Thr Asp Trp Ile Phe Ser His Pro
    130                 135                 140

Glu Ala Ser Thr Ser Ala Ser Ala Asp Ser Ser Thr Ser Asn Val Asn
145                 150                 155                 160

Ala Asp Asp Thr Tyr Ile Pro Asp Gly Ser Gly Arg Tyr Lys Leu Met
                165                 170                 175

Ala Phe Val Ser His Met Gly Ser Thr His Cys Gly His Tyr Val
            180                 185                 190

```
<210> SEQ ID NO 11
<211> LENGTH: 2018
<212> TYPE: DNA
<213> ORGANISM: Glycine max
<220> FEATURE:
<221> NAME/KEY: unsure
<222> LOCATION: (17)
<221> NAME/KEY: unsure
<222> LOCATION: (19)
<221> NAME/KEY: unsure
<222> LOCATION: (46)
<221> NAME/KEY: unsure
<222> LOCATION: (50)
<221> NAME/KEY: unsure
<222> LOCATION: (80)..(81)
<221> NAME/KEY: unsure
<222> LOCATION: (113)
<221> NAME/KEY: unsure
<222> LOCATION: (127)
<221> NAME/KEY: unsure
<222> LOCATION: (158)
```

-continued

```
<221> NAME/KEY: unsure
<222> LOCATION: (190)
<221> NAME/KEY: unsure
<222> LOCATION: (302)
<221> NAME/KEY: unsure
<222> LOCATION: (308)
<221> NAME/KEY: unsure
<222> LOCATION: (324)
<221> NAME/KEY: unsure
<222> LOCATION: (348)
<221> NAME/KEY: unsure
<222> LOCATION: (364)
<221> NAME/KEY: unsure
<222> LOCATION: (425)
<221> NAME/KEY: unsure
<222> LOCATION: (435)
<221> NAME/KEY: unsure
<222> LOCATION: (442)

<400> SEQUENCE: 11
tgggctatag gggttgntng gggatttgat aacaatggag ccacantatn aggaaaccca      60
tcagcgtagt tatattaccn ngagtatgtt tctcttccat tcccttctgt ggnattgcca     120
agagaangta ggctgggaag ttgatgcaat cctactanct gagggtggtg aacgaaagga     180
gcacttgcan catggactgc ctgataaaga agaaaaaatg tggggtggaa ctgggcggaa     240
acaaccatgc tgttgagcat taccaagaga cacgcttccc tgttgctgta aagcttggaa     300
cnatcacngc tgatcctgaa gcancaaatg tttactctta tccaaatnat gaaagtgtct     360
tggntccaca attagcgcag catctggcaa ttttttgggat tgacttttca tcactacgaa     420
agacngaaat gcaanctgct gnaaagagac ttgatcaaaa tacgaatttt gattggaatc     480
gaatccaaga aagtggacaa gaagtagatc caatttttgg acctggatat acaggattgg     540
tcaatattgg aaacagttgt tacatggcag caactatgca agttgtgttt tcaacaagat     600
ccttcacatc acggtactat ttgaaccaaa gtctaaagaa ggcatttgag atgtctcctg     660
ctgatcccac tgtagaccta aatatgcagt taacaaaatt ggctcacggc atactttctg     720
gtaaatattc tgttccggca tttgagaatg atgaaaaaga aaatgttgct acttcaacta     780
caactgctaa caagaaggg atacgtccac atatgtttaa atctgtaata gctgccagcc     840
atcctgaatt tcatctccg aggcaacagg atgctttaga attttttccta cattttcttg     900
atcaagttga gcgagctaat gctgggaaag ttgaactgga tccatcgacg agtttcaaat     960
ttggtattga agatagaatt ttgtgttcat ctggaaaagt tacatataat agaaggcatg    1020
actacattct ttctctcaat atcccattac atgaggcaac taacaaagaa gaattagaat    1080
cctttcacaa actgaaagca gagaaacttg cagaaggaaa ggaaataaat gccaatgaga    1140
ttgtgcgtcc aagggtacct ttagaaactt gccttgcgaa tttctcagct cctgaggaga    1200
tacatgattt ttacagtact gctttgaaga caaagacaac agcactgaag actgcaggtc    1260
tgacctcatt tcctgattac ctggtgttac atatgcggga atttgttatg gaggcagatt    1320
gggtaccaaa aaagcttgat gtgtacattg atgttcctga tatcatagat atcagtcaca    1380
tgcgcagcaa aggtcagcag tctggggaag agctattacc tgatggtgtt cctgaagagg    1440
aagattcaaa caaaatttcg gccaacgatg aaattgttgc ccagctggtt tccatgggct    1500
ttaaccatct ccattgtcag aaagctgcta taaatacatc caatgttgga gtagaagagg    1560
caatgaattg gttgctatct cacatggatg atccagacat tgacaatcct atttccaaag    1620
gccatggctc tgaaactgtt gaccaatcaa agttgatat tctaatttct tttggatttg    1680
aagaagaaat tgctaggaag gctctgaagg catcggatgg tgacattgag aaagcaacgg    1740
```

-continued

```
attggatatt taacaatctc gatgcatcag tctccagtat gaatgctgcc ccatcaacct    1800
ctgcatccac taccaatgat gttaacctac ccgatggagg agggaaatat cgacttatgg    1860
ggattgtgag ccacagtgga acttctacgc agtgtggcca ctatgttgct cacattttaa    1920
aagatggtag atgggcaatt ttcaacgaca acaaggtcgg ggcatccatt gatcctccaa    1980
aggaaatggg ctatctttat ttcttcgaaa ggctttga                            2018
```

<210> SEQ ID NO 12
<211> LENGTH: 594
<212> TYPE: PRT
<213> ORGANISM: Glycine max
<220> FEATURE:
<221> NAME/KEY: UNSURE
<222> LOCATION: (31)
<221> NAME/KEY: UNSURE
<222> LOCATION: (39)
<221> NAME/KEY: UNSURE
<222> LOCATION: (44)
<221> NAME/KEY: UNSURE
<222> LOCATION: (68)
<221> NAME/KEY: UNSURE
<222> LOCATION: (70)

<400> SEQUENCE: 12

```
Gly Gly Asn Asn His Ala Val Glu His Tyr Gln Glu Thr Arg Phe Pro
  1               5                  10                  15

Val Ala Val Lys Leu Gly Thr Ile Thr Ala Asp Pro Glu Ala Xaa Asn
             20                  25                  30

Val Tyr Ser Tyr Pro Asn Xaa Glu Ser Val Leu Xaa Pro Gln Leu Ala
         35                  40                  45

Gln His Leu Ala Ile Phe Gly Ile Asp Phe Ser Ser Leu Arg Lys Thr
     50                  55                  60

Glu Met Gln Xaa Ala Xaa Lys Arg Leu Asp Gln Asn Thr Asn Phe Asp
 65                  70                  75                  80

Trp Asn Arg Ile Gln Glu Ser Gly Gln Glu Val Asp Pro Ile Phe Gly
                 85                  90                  95

Pro Gly Tyr Thr Gly Leu Val Asn Ile Gly Asn Ser Cys Tyr Met Ala
            100                 105                 110

Ala Thr Met Gln Val Val Phe Ser Thr Arg Ser Phe Thr Ser Arg Tyr
        115                 120                 125

Tyr Leu Asn Gln Ser Leu Lys Lys Ala Phe Glu Met Ser Pro Ala Asp
    130                 135                 140

Pro Thr Val Asp Leu Asn Met Gln Leu Thr Lys Leu Ala His Gly Ile
145                 150                 155                 160

Leu Ser Gly Lys Tyr Ser Val Pro Ala Phe Glu Asn Asp Glu Lys Glu
                165                 170                 175

Asn Val Ala Thr Ser Thr Thr Thr Ala Lys Gln Glu Gly Ile Arg Pro
            180                 185                 190

His Met Phe Lys Ser Val Ile Ala Ala Ser His Pro Glu Phe Ser Ser
        195                 200                 205

Pro Arg Gln Gln Asp Ala Leu Glu Phe Phe Leu His Phe Leu Asp Gln
    210                 215                 220

Val Glu Arg Ala Asn Ala Gly Lys Val Glu Leu Asp Pro Ser Thr Ser
225                 230                 235                 240

Phe Lys Phe Gly Ile Glu Asp Arg Ile Leu Cys Ser Ser Gly Lys Val
                245                 250                 255

Thr Tyr Asn Arg Arg His Asp Tyr Ile Leu Ser Leu Asn Ile Pro Leu
            260                 265                 270
```

```
His Glu Ala Thr Asn Lys Glu Leu Glu Ser Phe His Lys Leu Lys
            275                 280                 285
Ala Glu Lys Leu Ala Glu Gly Lys Glu Ile Asn Ala Asn Glu Ile Val
290                 295                 300
Arg Pro Arg Val Pro Leu Glu Thr Cys Leu Ala Asn Phe Ser Ala Pro
305                 310                 315                 320
Glu Glu Ile His Asp Phe Tyr Ser Thr Ala Leu Lys Thr Lys Thr Thr
                325                 330                 335
Ala Leu Lys Thr Ala Gly Leu Thr Ser Phe Pro Asp Tyr Leu Val Leu
            340                 345                 350
His Met Arg Arg Phe Val Met Glu Ala Asp Trp Val Pro Lys Lys Leu
            355                 360                 365
Asp Val Tyr Ile Asp Val Pro Asp Ile Ile Asp Ile Ser His Met Arg
            370                 375                 380
Ser Lys Gly Gln Gln Ser Gly Glu Glu Leu Leu Pro Asp Gly Val Pro
385                 390                 395                 400
Glu Glu Asp Ser Asn Lys Ile Ser Ala Asn Asp Glu Ile Val Ala
                405                 410                 415
Gln Leu Val Ser Met Gly Phe Asn His Leu His Cys Gln Lys Ala Ala
            420                 425                 430
Ile Asn Thr Ser Asn Val Gly Val Glu Glu Ala Met Asn Trp Leu Leu
            435                 440                 445
Ser His Met Asp Asp Pro Asp Ile Asp Asn Pro Ile Ser Lys Gly His
            450                 455                 460
Gly Ser Glu Thr Val Asp Gln Ser Lys Val Asp Ile Leu Ile Ser Phe
465                 470                 475                 480
Gly Phe Glu Glu Glu Ile Ala Arg Lys Ala Leu Lys Ala Ser Asp Gly
                485                 490                 495
Asp Ile Glu Lys Ala Thr Asp Trp Ile Phe Asn Asn Leu Asp Ala Ser
            500                 505                 510
Val Ser Ser Met Asn Ala Ala Pro Ser Thr Ser Ala Ser Thr Thr Asn
            515                 520                 525
Asp Val Asn Leu Pro Asp Gly Gly Lys Tyr Arg Leu Met Gly Ile
            530                 535                 540
Val Ser His Ser Gly Thr Ser Thr Gln Cys Gly His Tyr Val Ala His
545                 550                 555                 560
Ile Leu Lys Asp Gly Arg Trp Ala Ile Phe Asn Asp Asn Lys Val Gly
                565                 570                 575
Ala Ser Ile Asp Pro Pro Lys Glu Met Gly Tyr Leu Tyr Phe Phe Glu
            580                 585                 590
Arg Leu
```

<210> SEQ ID NO 13
<211> LENGTH: 1200
<212> TYPE: DNA
<213> ORGANISM: Triticum aestivum

<400> SEQUENCE: 13

```
ctggaggcat gcttagcaag tttttcaggc ggagaggaag tgcctgagtt ttacagcact      60
gcattaaatt caaagacgac agcaattaag actactggcc ttaaaacttt tcctgattac    120
ctggtgcttc agatgcgtaa gtttgtaatg ggagaaggat gggtgccaaa gaaacttgat    180
gtttatattg acgtgccgga tataatcgat atctcgcaca tgcgcagcaa tggtgtacag    240
```

-continued

```
cctggggaag agctactgcc tgaaggagct tcttgtggca acaaagctga acctgctcgt    300
cctgttgccg acgaggatat tgtatcccag cttgcaaaca tcgggttcaa ttactttgcc    360
tgtcagaaag ctgctattaa tacatcaaat gcaggacttg aggaggcaat gaattggctc    420
ctctcacaca cgcaggatcc agatattaat gagccgatat ctcaagatcc aatgcctgca    480
gaagacacta ttgatgaagc aagtcttcaa actcttgttt cctttggctt tccagaagat    540
gtttcccgaa tggccttgaa agcttccggt ggaaatattg agagagccac ggagtgggtt    600
ttcagccacc ctgaagcatc tagctctgta tctgctgact cttcaacaaa caatgtaaaa    660
gatgacgact cgcacatatc agatggaagt ggcagataca agctgatggc atttgtgagc    720
cacatgggaa cctctacaca ctgtgggcac tatgtcgccc atatcctcaa agatgggagg    780
tggacgatct tcaatgacaa taaggttgct gcatcggtcg acctgcccaa ggacatggga    840
tacctctatt tctttcagag gataagcagt tagagcagaa gatgaagtcg tagttcatgc    900
atgcatatca tccaggagca tggcggatgc tcgaaggact attgcaaatc tgacttgaag    960
cgaccacttc gccacatcct gacgtgctgg tcttaggctg atcacgtggg ataccgcttt   1020
gttggttcag acgttatatg cattggcaac ttcctttacg tttatgctta gtaccatgtg   1080
acactgttca tgcaaagtga atggttgtgt ttggagtcgt acaatctgtc agcgttccgt   1140
tggtttctta ctttcttata gttggaattt tattcgagca aaaaaaaaa aaaaaaaaa    1200
```

<210> SEQ ID NO 14
<211> LENGTH: 290
<212> TYPE: PRT
<213> ORGANISM: Triticum aestivum

<400> SEQUENCE: 14

```
Leu Glu Ala Cys Leu Ala Ser Phe Ser Gly Glu Glu Val Pro Glu
  1               5                  10                  15

Phe Tyr Ser Thr Ala Leu Asn Ser Lys Thr Thr Ala Ile Lys Thr Thr
                 20                  25                  30

Gly Leu Lys Thr Phe Pro Asp Tyr Leu Val Leu Gln Met Arg Lys Phe
             35                  40                  45

Val Met Gly Glu Gly Trp Val Pro Lys Lys Leu Asp Val Tyr Ile Asp
     50                  55                  60

Val Pro Asp Ile Ile Asp Ile Ser His Met Arg Ser Asn Gly Val Gln
 65                  70                  75                  80

Pro Gly Glu Glu Leu Leu Pro Glu Gly Ala Ser Cys Gly Asn Lys Ala
                 85                  90                  95

Glu Pro Ala Arg Pro Val Ala Asp Glu Asp Ile Val Ser Gln Leu Ala
            100                 105                 110

Asn Ile Gly Phe Asn Tyr Phe Ala Cys Gln Lys Ala Ala Ile Asn Thr
        115                 120                 125

Ser Asn Ala Gly Leu Glu Glu Ala Met Asn Trp Leu Leu Ser His Thr
130                 135                 140

Gln Asp Pro Asp Ile Asn Glu Pro Ile Ser Gln Asp Pro Met Pro Ala
145                 150                 155                 160

Glu Asp Thr Ile Asp Glu Ala Ser Leu Gln Thr Leu Val Ser Phe Gly
                165                 170                 175

Phe Pro Glu Asp Val Ser Arg Met Ala Leu Lys Ala Ser Gly Gly Asn
            180                 185                 190

Ile Glu Arg Ala Thr Glu Trp Val Phe Ser His Pro Glu Ala Ser Ser
        195                 200                 205
```

```
Ser Val Ser Ala Asp Ser Ser Thr Asn Asn Val Lys Asp Asp Ser
    210                 215                 220

His Ile Ser Asp Gly Ser Gly Arg Tyr Lys Leu Met Ala Phe Val Ser
225                 230                 235                 240

His Met Gly Thr Ser Thr His Cys Gly His Tyr Val Ala His Ile Leu
                245                 250                 255

Lys Asp Gly Arg Trp Thr Ile Phe Asn Asp Asn Lys Val Ala Ala Ser
            260                 265                 270

Val Asp Leu Pro Lys Asp Met Gly Tyr Leu Tyr Phe Phe Gln Arg Ile
        275                 280                 285

Ser Ser
    290

<210> SEQ ID NO 15
<211> LENGTH: 534
<212> TYPE: DNA
<213> ORGANISM: Triticum aestivum
<220> FEATURE:
<221> NAME/KEY: unsure
<222> LOCATION: (88)
<221> NAME/KEY: unsure
<222> LOCATION: (492)
<221> NAME/KEY: unsure
<222> LOCATION: (529)
<221> NAME/KEY: unsure
<222> LOCATION: (534)

<400> SEQUENCE: 15
agaaagttaa gctcgcaatt gataaagtta tacttgcggg agagtgctga taaaaagcaa      60
caactgggct tcttgggtgg ctgacaanaa aattatcaag tgcacatgct atggatctgc     120
aacaactaaa caatggtgtt attgtgcccc ctaccgggtg gaaagtgtag caagtgtgac     180
aaaactgaga atctctggtt aaatttaact gatggtatga tcctctgtgg gaggtgggtc     240
tgggatggaa ctggtggaaa taatcatgct gttgaacact accaacagac taaatatcct     300
ttagcggtga agcttggaac aattactgct gatttggaag gagcaaacgt ttactcatac     360
ccggaagatg ataagcgtcc gaagattcaa tatttagctc agcacttgtc gcaatttggg     420
attgattttt cctcactcca aaaagactga gatgactact gctgaaaaga gaactttgac     480
cacaacacta anttttgatt tgggaataag aaatacaaag aaagtgggna aagn           534

<210> SEQ ID NO 16
<211> LENGTH: 116
<212> TYPE: PRT
<213> ORGANISM: Triticum aestivum

<400> SEQUENCE: 16

Ser Ala His Ala Met Asp Leu Gln Gln Leu Asn Asn Gly Val Ile Val
1               5                   10                  15

Pro Pro Thr Gly Trp Lys Cys Ser Lys Cys Asp Lys Thr Glu Asn Leu
            20                  25                  30

Trp Leu Asn Leu Thr Asp Gly Met Ile Leu Cys Gly Arg Trp Val Trp
        35                  40                  45

Asp Gly Thr Gly Gly Asn Asn His Ala Val Glu His Tyr Gln Gln Thr
    50                  55                  60

Lys Tyr Pro Leu Ala Val Lys Leu Gly Thr Ile Thr Ala Asp Leu Glu
65                  70                  75                  80

Gly Ala Asn Val Tyr Ser Tyr Pro Glu Asp Asp Lys Arg Pro Lys Ile
                85                  90                  95
```

```
                                  -continued

Gln Tyr Leu Ala Gln His Leu Ser Gln Phe Gly Ile Asp Phe Ser Ser
            100                 105                 110

Leu Gln Lys Asp
        115
```